US006838053B2

(12) United States Patent
John et al.

(10) Patent No.: US 6,838,053 B2
(45) Date of Patent: Jan. 4, 2005

(54) PLATINUM SILICIDE PERMEATION LAYER DEVICE WITH MICROLOCAIONS

(75) Inventors: Havens R. John, San Diego, CA (US); Theodore M. Winger, San Diego, CA (US); Jain Krotz, San Diego, CA (US); Smolko Dan, Jamul, CA (US); Thomas J. Onofrey, San Marcos, CA (US)

(73) Assignee: Nanogen, Inc., San Diego, CA (US)

( * ) Notice: Subject to any disclaimer, the term of this patent is extended or adjusted under 35 U.S.C. 154(b) by 103 days.

(21) Appl. No.: 09/922,349

(22) Filed: Aug. 3, 2001

(65) Prior Publication Data

US 2002/0015993 A1 Feb. 7, 2002

Related U.S. Application Data

(62) Division of application No. 09/464,670, filed on Dec. 15, 1999, now Pat. No. 6,303,082.

(51) Int. Cl.[7] .............................................. G01N 15/06
(52) U.S. Cl. ........................ 422/68.1; 422/50; 422/129; 435/6; 435/7.1
(58) Field of Search ........................ 435/7.1, 6; 422/50, 422/68.1, 129

(56) References Cited

U.S. PATENT DOCUMENTS

| | | |
|---|---|---|
| 3,981,671 A | 9/1976 | Edwards |
| RE30,130 E | 10/1979 | Edwards |
| 4,205,028 A | 5/1980 | Brueggemann et al. |
| 4,284,399 A | 8/1981 | Newcomb et al. |
| 4,497,763 A | 2/1985 | Monnet |
| 4,552,633 A | 11/1985 | Kumakura et al. |
| 4,787,963 A | 11/1988 | MacConnell |
| 4,897,228 A | 1/1990 | Miwa et al. |
| 5,026,785 A | 6/1991 | Mage et al. |
| 5,034,428 A | 7/1991 | Hoffman et al. |

(List continued on next page.)

FOREIGN PATENT DOCUMENTS

| | | |
|---|---|---|
| EP | 0047645 B1 | 11/1984 |
| EP | 0 226 470 A2 | 6/1987 |
| EP | 0243501 A1 | 11/1987 |
| JP | 55-152027 A | 11/1980 |
| JP | 56-167419 A | 12/1981 |
| JP | 59-215838 A | 12/1984 |
| JP | 59-227131 A | 12/1984 |
| JP | 01163040 A | 6/1989 |
| JP | 02292013 A | 12/1990 |

OTHER PUBLICATIONS

Brinker et al., Sol–Gel Science, Academic Press, San Diego, 1990.

Vasiliskov, A.V., Timofeev, E.N., Surzhikov, S.A., Drobyshev, A.L., Shick, V.V., Mirzabekov, A.D., "Febrication of Microarray of Gel–Immobilized Compounds on a Chip by Copolymerization," Bio Techniques, vol. 27, pp. 592–606 (Sep. 1999).

Anderson et al, Polymerized Lyotropic Liquid Crystals As Contact Lens Materials, Physica A, 1991, 176, 151–167, Elsevier Science Publishers B.V. (North Holland).

(List continued on next page.)

Primary Examiner—Ardin H. Marschel
(74) Attorney, Agent, or Firm—O'Melveny & Myers LLP

(57) ABSTRACT

Electronically addressable microchips having covalently bound permeation layers and methods of making such covalently bonded permeation layers to microchips are provided. The covalent bonding is derived from combining the use of electrodes with silane derivatives. Such chemistry provides the ability to apply an electronic bias to the electrodes of the microchip while preventing permeation layer delaminating from the electrode surface.

22 Claims, 10 Drawing Sheets

U.S. PATENT DOCUMENTS

| | | |
|---|---|---|
| 5,104,931 A | 4/1992 | Fleminger et al. |
| 5,147,297 A | 9/1992 | Myers et al. |
| 5,151,217 A | 9/1992 | Price |
| 5,164,162 A | 11/1992 | Ridenour |
| 5,171,782 A | 12/1992 | Candau et al. |
| 5,217,492 A | 6/1993 | Guire et al. |
| 5,238,613 A | 8/1993 | Anderson |
| 5,244,799 A | 9/1993 | Anderson |
| 5,334,310 A | 8/1994 | Frechet et al. |
| 5,405,618 A | 4/1995 | Buttery et al. |
| 5,445,934 A | 8/1995 | Fodor et al. |
| 5,453,185 A | 9/1995 | Frechet et al. |
| 5,460,872 A | 10/1995 | Wu et al. |
| 5,478,893 A | 12/1995 | Ghosh et al. |
| 5,496,509 A | 3/1996 | Yamamoto et al. |
| 5,510,074 A | 4/1996 | Rose |
| 5,521,229 A | 5/1996 | Lu et al. |
| 5,527,670 A | 6/1996 | Stanley et al. |
| 5,534,132 A | 7/1996 | Vreeke et al. |
| 5,543,098 A | 8/1996 | Myers et al. |
| 5,605,662 A | 2/1997 | Heller et al. |
| 5,618,265 A | 4/1997 | Myers et al. |
| 5,624,973 A | 4/1997 | Lu et al. |
| 5,632,957 A | 5/1997 | Heller et al. |
| 5,648,482 A | 7/1997 | Meyer |
| 5,653,939 A | 8/1997 | Hollis et al. |
| 5,667,667 A | 9/1997 | Southern |
| 5,744,627 A | 4/1998 | Stowolitz et al. |
| 5,770,369 A | 6/1998 | Meade et al. |
| 5,777,148 A | 7/1998 | Stowolitz et al. |
| 5,783,054 A | 7/1998 | Raguse et al. |
| 5,849,486 A | 12/1998 | Heller et al. |
| 5,889,104 A | 3/1999 | Rosenmayer |
| 5,919,523 A | 7/1999 | Sundberg et al. |
| 5,929,208 A | 7/1999 | Heller et al. |
| 5,952,398 A | 9/1999 | Dietz et al. |
| 5,981,734 A | 11/1999 | Mirzabekov et al. |
| 6,015,666 A | 1/2000 | Springer et al. |
| 6,017,696 A | 1/2000 | Heller |
| 6,031,277 A | 2/2000 | Sugiura et al. |
| 6,039,897 A | 3/2000 | Lochhead et al. |
| 6,048,690 A | 4/2000 | Heller et al. |
| 6,051,380 A | 4/2000 | Sosnowski et al. ............ 435/6 |
| 6,054,270 A | 4/2000 | Southern |
| 6,064,461 A | 5/2000 | Nishida |
| 6,099,783 A | 8/2000 | Scranton et al. |
| 6,099,805 A | 8/2000 | Hartlove |
| 6,121,027 A | 9/2000 | Clapper et al. |
| 6,121,489 A | 9/2000 | Dorner et al. |
| 6,136,444 A | 10/2000 | Kon et al. |
| 6,143,412 A | 11/2000 | Schueller et al. |
| 6,197,145 B1 | 3/2001 | Todd et al. |
| 6,197,881 B1 | 3/2001 | Cosnier et al. |
| 6,245,249 B1 | 6/2001 | Yamada et al. |
| 6,245,508 B1 | 6/2001 | Heller et al. |
| 6,264,825 B1 | 7/2001 | Blackburn et al. |
| 6,303,082 B1 | 10/2001 | John et al. |
| 6,306,348 B1 | 10/2001 | Havens et al. |
| 6,444,111 B1 | 9/2002 | Montgomery |
| 6,458,584 B1 | 10/2002 | Mirzabekov et al. |
| 6,524,517 B1 | 2/2003 | John et al. |
| 6,615,855 B2 | 9/2003 | Lopez et al. |
| 6,673,433 B1 | 1/2004 | Saeki et al. |

OTHER PUBLICATIONS

Antonietti et al., Polymerization In Microemulsions–A New Approach To Ultrafine, Highly Functionalized Polymer Dispersion, Macromol.Chem.Phys., 1995, 196, 441–446, Hüthig & Wepf Verlag, Zug.

Antonietti et al, Morphology Variation Of Porous Polymer Gels By Polymerization in Lytropic Surfactant Phases, Macromolecules, 1999, 32, 1383–1389, American Chemical Society.

Antonietti et al, Polymer Gels With A Micron–sized, Layer–Like Architecture By Polymerization In Lyotropic Cocogem Phases, Langmuir, 1998, 14, 2670–2676, American Chemical Society.

Antonietti et al., Synthesis Of Sponge–Like Polymer Dispersions Via Polymerization Of Biocontinuous Microemulsions, Colloid Polym Sci, 1996, 274, 698–702, Steinkopff Verlag.

Antonietti et al., Microemulsions Polymerization: New Surfactant Systems By Counterion Variation, Adv. Mater., 1996, 8, 10, 840–844, VCH Vertagsgetlshaft mbH, Weinheim.

Arenkov et al, Protein Microchips: Use For Immunoassay & Enzymatic Reactions, Analytical Biochemistry, 2000, 278, 123–131, Academic Press.

Bates, Polymer–Polymer Phase Behavior, Science, Feb. 22, 1991, 25, 898–905.

Benedicto et al, Biocontinuous Cubic Morphologies In Block Copolymers & Amphiphile/Water Systems: Mathematical Description Through The Minimal Surfaces, Macromolecules, 1997, 30, 3395–3402, American Chemical Society.

Brown, Dot & Slot Blotting of DNA, Current Protocols in Molecular Biology, 1993, Supplement 21, 2.9.15–2.10.16.

Burban et al, Organic Microporous Materials Made By Biocontinuous Microemulsion Polymerization, AIChE Journal, Apr. 1995, 41, 4, 907–914.

Chieng et al., Microporous Polymeric Materials By Microemulsion Polymerization: Effect of Surfactant Concentrations, Langmuir, 1995, 11, 3321–3326.

Chieng et al., Morphology Of Microporous Polymeric Materials By Polymerization Of Methyl Methacrylate & 2–Hydroxyethyl Methacrylate In Microemulsions, Polymer, 1995, 36, 10, 1941–1946, Elsevier Science Ltd. Great Britain.

Chieng et al, Formation Of Microporous Polymeric Materials By Microemulsion Polymerization Of Methyl Methacrylate & 2–Hydroxyethyl Methacrylate, Journal of Applied Polymer Science, 1996, 60, 1561–1568, John Wiley & Sons, Inc.

Hentze et al, Synthesis Of Organic Polymer Gels in Microemulsions & Lyotropic Mesophases, Ber.Bunsenges. Phys. Chem., 1997, 101, 11, 1699–1702, Wiley–VCH, Weinheim.

Hermanson, *Bioconiugate Techniques*, Academic Press, San Diego, California, 1996, table of contents only.

Kempe et al, Receptor Binding Mimetics: A Novel Molecularly Imprinted Polymer, Tetrahedron Letters, 1995, 36, 20, 3563–3566.

Lee et al., Polymerization Of Nonlamellar Lipid Assemblies, J. Am. Chem. Soc., 1995, 117, 5573–5578.

Lindblom et al, Cubic Phases & Isotropic Structures Formed By Membrane Lipids–Possible Biological Relevance, Biochimica et Biophysics Acta, 1989, 988, 221–256, Elsevier Science Publishers B.V. (Biomedical Div).

O'Connell et al, Polyacrylamide Gels With Modified Cross–Linkages, Analytical Biochemistry, 1976, 76, 63–73, Academic Press, Inc.

Odian, *Principles of Polymerization*, 3$^{rd}$ Edition, John Wiley & Sons, New York, New York, 1991, 232.

Paul et al, Cubic Polymer Hydrogels: Templated Polymerization from Surfactant Mesophases, AIChE Meeting, Dallas, Texas, Oct. 31–Nov. 5, 1999, 71.

Peters et al, Rigid Macroporous Polymer Monoliths, Adv. Mater, 1999, 11, 14, 1169–1181, Wiley–VCH, Weinheim.

Raj et al, Formation of Porous Polymeric Structures By The Polymerization Of Single–Phase Microemulsions Formulated with Methyl Methacrylate & Acrylic Acid, Langmuir, 1991, 7, 2586–2591, American Chemical Society.

Raj et al, Polymerization Of Microstructured Aqueous Systems Formed Using Methyl Methacrylate & Potassium Undeconoate, Langmuir, 1992, 8, 1931–1936.

Raj et al, Synthesis Of Porous Polymeric Membranes By Polymerization Of Micro–emulsions, Polymer, 1993, 34, 15, 3305–3312, Butterworth–Heinemann Ltd.

Raj et al, Microcellular Polymeric Materials From Microemulsions: Control Of Microstruture & Morphology, Journal Of Applied Polymer Science, 1993, 47, 499–511, John Wiley & Sons, Inc.

Righetti et al., On The Limiting Pore Size Of Hydrophilic Gels For Electrophoresis & Isoelectric Focusing, Journal Of Biochemical & Biophysical Methods, 1981, 4, 347–363.

Righetti et al., Towards New Formulations For Polyacrylamide Matrices, As Investigated By Capillary Zone Electrophoresis, Journal Of Chromatography, 1993, 638, 165–178, Elsevier Science Publishers B.V.

Rill et al, Templated Pores in Hydrogels For Improved Size Selectivity in Gel Permeation Chromatography, Analytical Chemistry, Jul. 1, 1998, 70, 13, 2433–2438.

Samal et al., Electroinitiated Polymerization Of Acrylamide in Acetonitrite Medium, J. Polym. Sci. Polym. Chem., 26, 1988, 1035–1049.

Sasthav et al, Characterization Of Microporous Polymeric Materials: Pore Continuity & Size Distribution Via Thermal Analysis, Journal Of Colloid & Interface Science, Sep. 1992, 152, 2, 376–385.

Seddon, Structure Of The Inverted Hexagonal ($H_{11}$)Phase, & Non–Lamellar Phase Transitions Of Lipids, Biochimica et Biophysica Acta, 1990, 1031, 1–69, Elsevier Science Publishers BV (Biomedical Div).

Shiyakhtenko et al., Atomic Force Microscopy Imaging Of DNA Covalently Immobilized On A Functionalized Mica Substrate, Biophysical Journal, Jul. 1999, 77, 568–576, Biophysical Society.

Sosnowshi et al., Rapid Determination Of Single Base Mismatch Mutations in DNA Hybrids By Direct Electric Field Control, Proc. Natl. Acad. Sci. USA, Feb. 1997, 94, 1119–1123.

Srisiri et al, Polymerization Of The Inverted Hexagonal Phase, J. Am. Chem. Soc., 1997, 119, 4866–4873, American Chemical Society.

Svec et al, Molded Rigid Monolithic Porous Polymers: An Inexpensive, Efficient & Versatile Alternative To Beads For The Design Of Materials For Numerous Applications, Ind. Eng. Chem. Res., 1999, 38, 34–48, American Chemical Society.

Viklund et al, Monolithic, "Molded", Porous Materials With High Flow Characteristics For Separations, Catalysis, Or Solid–Phase Chemistry: Control Of Porous Properties During Polymerization, Chem. Mater., 1996, 8, 744–750, American Chemical Society.

PLATINUM SILICIDE PERMEATION LAYER DEVICE WITH MICROLOCAIONS

This application is a division of Ser. No. 09/464,670 filed Dec. 15, 1999 now U.S. Pat. No. 6,303,082.

FIELD OF THE INVENTION

This invention relates to the attachment of a layer of polymeric material to a substrate surface. More particularly, this invention relates to chemistries and methods for covalently attaching a porous polymeric material to an electrically conductive substrate, such as a metal electrode of a microchip circuit.

BACKGROUND OF THE INVENTION

The following description provides a summary of information relevant to the present invention. It is not an admission that any of the information provided herein is prior art to the presently claimed invention, nor that any of the publications specifically or implicitly referenced are prior art to the invention.

In the art of electronically addressable microchips that are used to direct biomaterials, such as nucleic acids and proteins, from one point in a solution to another, the microchips should be designed so that electric potential from the microchip electrodes will translate to the solution overlying the microchip such that any electrochemistry occurring from the electrode surface will neither damage the electrodes themselves, nor any biomaterials in the solution. Generally, protection from such damage is provided by the use of a porous membrane layer deposited over the microchip electrodes. Usually, such layer comprises materials derived from natural or synthetic polymers such as agarose or polyacrylamide, respectively. These types of materials allow electrochemical products generated at the electrode surface to travel through their porous matrix or 'permeation layer' and into the solution immediately above the electrodes.

Although materials such as those noted above have been found useful in the role of a porous membrane having desired qualities, it has been found that because of the methodologies commonly used to layer such membranes onto the microchip substrate, the membranes are prone to separate or 'delaminate' from the electrode surface. It is believed this delamination is caused by a change in the chemical make-up at the interface between the permeation layer and the electrode resulting from the application of electronic potential at the electrode and by physical disruption from charged ions and gases emanating from the electrode. Such delamination can be viewed from the standpoint of 'microdelamination' and 'macrodelamination'.

Microdelamination involves the electrochemical degradation of the chemical interface between the permeation layer and the electrode itself. It is observed by the formation of raised bulges in the permeation layer, or by ringlets visible due to defraction of light from the delaminated layer when appropriately viewed by a confocal microscope and results in the loss of consistency in permeation layer performance (possibly due to the loss of control over the electric field uniformity). Macrodelamination, on the other hand, is caused by a mismatch of the surface energies between the permeation layer and the chip substrate and results in permeation layer peeling (lift-off) which can extend across the entire microchip surface. Since the permeation layer provides a means for chemical anchorage of analytes present in the liquid overlay, its physical loss by macrodelamination results in catastrophic chip failure during bioassays.

Electronically addressable systems such as the microchips considered herein follow Ohm's law which establishes the relationship between the voltage drop (V) between two electrodes (i.e., the anode, placed at a positive potential and the other, the cathode, placed at a negative potential), and the electric current (I) which flows between these electrodes, as follows:

$$V = R \times I \qquad (1)$$

where R is the electrical resistance of the medium between the anode and the cathode. In systems where a permeation layer is present over such electrodes, the value of R is greatly determined by the physical and chemical nature of said permeation layer. Thus, according to formula (1), the difference between the electronic potentials applied to the electrodes is directly proportional to the intensity or density of the electric current which flows through them. The invention described in this Letters Patent uses a relationship between electric current and voltage wherein electric current densities are at least 0.04 nA/$\mu$m$^2$ and/or voltage drops are between 1 and 3 V. The electric current density is defined as the electric current divided by the area of the electrode used to support it.

Additionally, the effectiveness of the translocation of charged biomolecules such as nucleotide oligomers within an electronically-driven system such as that described herein depends on the generation of the proper gradient of positively and negatively charged electrochemical species by the anode and cathode, respectively. For example, effective nucleic acid (i.e. either DNA or RNA) transport may be accomplished by generation of protons and hydroxyl anions when the potential at the anode is greater than +1.29 V with respect to a 'saturated calomel electrode' (SCE). When subjected to such demanding operating conditions, noncovalently-attached permeation layers prove to be unsatisfactory since such systems are likely to experience micro- and sometimes macrodelamination. Moreover, the transport efficiency of charged molecules increases with increasing current density, thus driving the desire for operation at higher voltage drops and current densities and, thus, the need for evermore robust permeation layers.

Therefore, a need still remains for methodologies for keeping permeation layers from delaminating from electronic microchip substrates and particularly from the electrode pads themselves. We have discovered an improvement in permeation layer attachment chemistry that provides a significant increase in permeation layer performance. Specifically, we have solved the problem of micro- and macrodelamination by discovery of a covalent chemistry linkage system that, as applied to electronically addressable microchip art, can be incorporated between the microchip and the permeation layer matrix. This chemistry is applicable to a variety of permeation layer compositions, including polymers, hydrogels, glyoxylagarose, polyacrylamide, polymers of methacrylamide, materials made from other synthetic monomers, and porous inorganic oxides created through a sol-gel process, and is able to withstand current densities of at least 0.04 nA/$\mu$m$^2$ and/or voltage drops between 1 and 3 V.

SUMMARY OF THE INVENTION

The current invention provides a unique system for the covalent attachment of a porous 'permeation layer' to the surface of electronically addressable microchips. In a preferred embodiment, the covalent attachment is between chemical moieties of the permeation layer and metal/ silicide, metal/metal, or organic electrodes. Preferred metal/silicide electrodes include platinum silicide (PtSi), tungsten silicide (WTi), titanium silicide (TiSi), and gold silicide (AuSi). Preferred metal/metal electrodes include platinum/titanium (PtTi) and gold/titanium (AuTi). Preferred organic electrodes include materials such as poly(phenylene vinylene), polythiophene, and polyaniline.

In an example of this embodiment, the covalent attachment comprises a linking moiety that provides an attachment mechanism for bonding the linker to the silanol moiety of a metal/Si surface and a separate moiety for bonding the linker to the permeation layer. Where metal/metal and organic electrodes are employed, the attachment mechanism of the linker to the electrode is the same in that the moiety of the linker attaching to the electrode will react with specific metals and reactive centers on organic molecules to form covalent bonds.

In a particularly preferred embodiment, the linking moiety is defined by the formula:

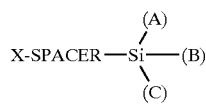

where X=acrylate, methacrylate, acrylamide, methacrylamide, allyl, vinyl, acetyl, amine (substituted or not), epoxy or thiol;

SPACER=alkyl, aryl, mono- or polyalkoxy (such as ethyleneglycol or polyethyleneglycol), mono- or polyalkylamine, mono- or polyamide, thioether derivatives, or mono- or polydisulfides;

A and B=any combination of Oxygen-R, where R=H, alkyl such as methyl, ethyl, propyl, isopropyl or other linear or branched hydrocarbon, Cl, Br or a moiety functionality similar to that of X-SPACER; and C=Oxygen-R, where R=H, alkyl such as methyl, ethyl, propyl, isopropyl or other linear or branched hydrocarbon, Cl, Br, or any other hydrolyzable moiety.

In the example of the metal/Si electrodes, these linkage groups, which contain a suicide group can react with hydroxyl groups bonded to an oxygen moiety of the electrode surface. On the other end of the linker, the X moiety comprises chemical groups that are available to covalently react with reactive centers of the permeation layer polymer.

In another embodiment, the permeation layer is a material suitable for transmitting electronic charge from an electrode to a solution overlaying the electrode. Materials contemplated for constructing polymers used for the permeation layer may include, but are not limited to, agarose, glyoxylagarose, acrylamide, methacrylamide, polyacrylamide, materials made from other synthetic monomers, hydrogels, and porous inorganic oxides created through a sol-gel process (Brinker et al., *Sol-Gel Science*, Academic Press, San Diego, 1990).

Synthetic monomers used to make polymeric permeation layers may include those selected from the group consisting of epoxides, alkenyl moieties including, but not limited to, substituted or unsubstituted α, β unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; and alkynyl moieties wherein a triple bond exists between two carbon atoms.

In another embodiment, the covalently attached permeation layer is kept from delaminating while the anode is charged with an electronic potential above +1.29V/SCE and/or the cathode with a potential below −0.89 V/SCE. In a particularly preferred embodiment, the current flow between the electrodes has a density sufficient to induce the transport of molecules in the solution above the electrodes of the microchip. Such density is preferably at least 0.04 nA/$\mu$m$^2$.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee. The invention will be further described with reference to the accompanying drawings in which:

In FIG. 5A, the Pt electrode began to delaminate at the second direct current impulse of 500 nA (0.1 nA/$\mu$m$^2$) for 2 min. In contrast, (FIG. 5B) the PtSi electrode showed no delamination after the second direct current impulse of 500 nA (0.1 nA/$\mu$m$^2$).

In FIG. 8 the focal plane of the image is set at 3 μm above the electrode prior to electronic biasing. This indicates the permeation layer surface is 3 μm above the electrode as indicated by the beads being in focus. In FIG. 9 an unchanged focal plane during electronic biasing is shown. In FIG. 10, a focal plane 4 μm above the electrode is shown indicating that delamination occurred causing the permeation layer to rise so that the beads resting on top of the layer come into focus at a greater distance from the electrode.

FIG. 12 shows that the focal plane remained unchanged after a two-minute bias at +2 μA (0.4 nA/μm$^2$). FIG. 13 confirms that no delamination occurred with this electrode.

DETAILED DESCRIPTION OF THE PREFERRED EMBODIMENTS

In the art of electronically addressable microchips used for transporting charged molecules from one point in a solution to another, the transported molecules must be protected from direct contact with the electrodes of the microchip and ions produced at the electrode when the electrodes are biased to impart an electric field to the solution. Protection is provided by an insulating membrane, i.e., the permeation layer, which also allows for the flow of charge from the electrode to the solution without damaging the transported molecules. Typically, the insulating membrane is a polymeric material such as agarose or cross-linked polyacrylamide. These materials are ideal in that they are porous and allow electrochemical products created at the electrode to escape to the overlying solution.

More specifically, such insulating membrane materials can comprise, but are not limited to, agarose, glyoxylagarose, acrylamide, methacrylamide, polyacrylamide, materials made from other synthetic monomers, and porous inorganic oxides created through a sol-gel process. Synthetic monomers used to make polymeric permeation layers may also include those selected from the group consisting of epoxides, alkenyl moieties including, but not limited to, substituted or unsubstituted α, β unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; and alkynyl moieties wherein a triple bond exists between two carbon atoms.

Figure 1:
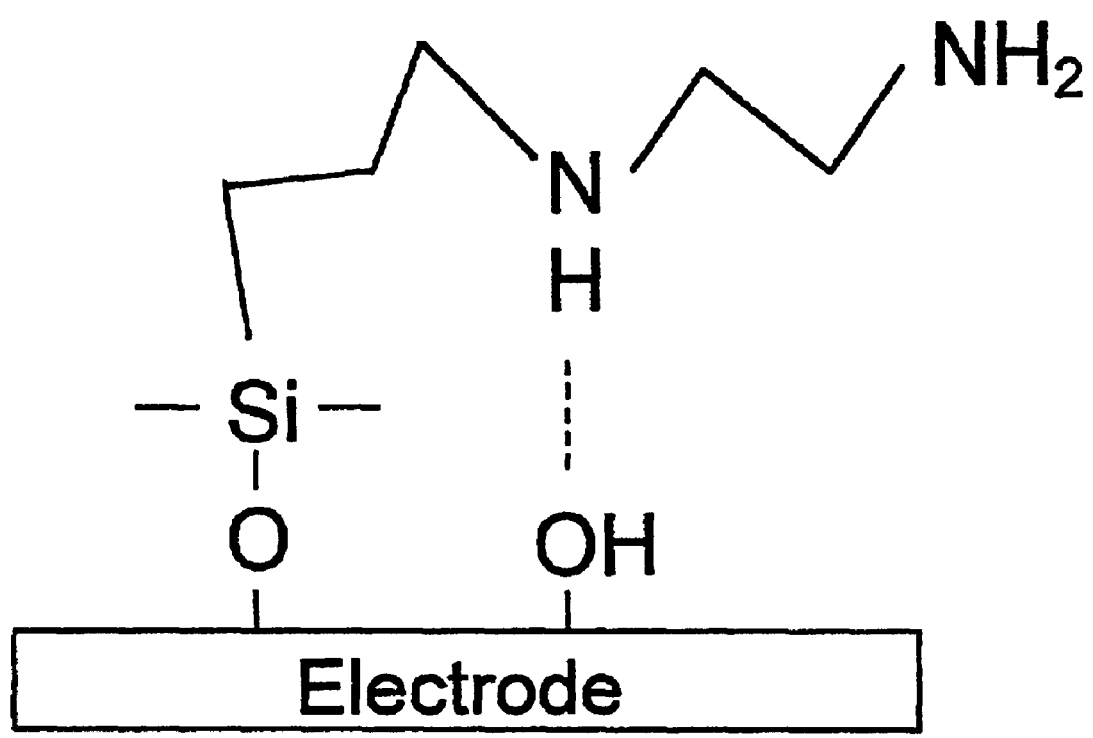
FIG. 1 is a chemical structure schematic showing attachment of a linker moiety to the electrode surface.

As described above, for optimal functionality of electronically addressable microchips, it is important that the porous insulating layer or permeation layer remain in contact with the electrode in order to enhance uniformity and consistency of the electronic potential from one pad to the other. As shown in FIG. 1 the permeation layer may be linked to the electrode by a linking moiety that has at least two reactive centers. Linkers having suitable characteristics such as that shown in FIG. 1 are provided in Table I.

TABLE I

| CHEMICAL TYPE | FORMULA |
|---|---|
| ACRYLATES: | $CH_2$=$CHCOOCH_2CH_2CH_2Si(OCH_3)_3$ |
| | $CH_2$=$CHCOOCH_2CH_2CH_2SiCl_3$ |
| | $CH_2$=$CHCOOCH_2CH_2CH_2Si(CH_3)(OCH_3)_2$ |
| | $CH_2$=$CHCOOCH_2CH_2CH_2Si(CH_3)_2(OCH_3)$ |
| | $CH_2$=$CHCOOCH_2CH_2CH_2Si(CH_3)Cl_2$ |
| | $CH_2$=$CHCOOCH_2CH(OH)CH_2NHCH_2CH_2CH_2Si(OC_2H_5)_3$ |
| METHACRYLATES: | $CH_2$=$C(CH_3)COOCH_2CH_2CH_2Si(OCH_3)_3$(MOTS) |
| | $CH_2$=$C(CH_3)COOCH_2CH_2CH_2SiCl_3$ |
| | $CH_2$=$C(CH_3)COOCH_2CH_2CH_2Si(CH_3)(OCH_3)_2$ |
| | $CH_2$=$C(CH_3)COOCH_2CH_2CH_2Si(CH_3)_2(OCH_3)$ |
| | $CH_2$=$C(CH_3)COOCH_2CH_2CH_2Si(CH_3)Cl_2$ |
| | $CH_2$=$C(CH_3)COOCH_2CH(OH)CH_2NHCH_2CH_2CH_2Si(OC_2H_5)_3$ |
| ACRYLAMIDES: | $CH_2$=$CHCONHCH_2CH_2CH_2Si(OC_2H_5)_3$(AMPTS) |
| | $CH_2$=$CHCONHCH_2CH_2CH_2SiCl_3$ |
| | $CH_2$=$CHCONHCH_2CH_2CH_2Si(CH_3)(OCH_3)_2$ |
| | $CH_2$=$CHCONHCH_2CH_2CH_2Si(CH_3)_2(OCH_3)$ |
| | $CH_2$=$CHCONHCH_2CH_2CH_2Si(CH_3)Cl_2$ |
| | $CH_2$=$CHCONHCH_2CH(OH)CH_2NHCH_2CH_2CH_2Si(OC_2H_5)_3$ |
| | $CH_2$=$CHCONHCH_2CH_2CONHCH_2CH_2CONHCH_2CH_2CH_2Si(OC_2H_5)_3$ |
| METHACRYLAMIDES: | $CH_2$=$C(CH_3)CONHCH_2CH_2CH_2Si(OCH_3)_3$ |
| | $CH_2$=$C(CH_3)CONHCH_2CH_2CH_2SiCl_3$ |
| | $CH_2$=$C(CH_3)CONHCH_2CH_2CH_2Si(CH_3)(OCH_3)_2$ |
| | $CH_2$=$C(CH_3)CONHCH_2CH_2CH_2Si(CH_3)_2(OCH_3)$ |
| | $CH_2$=$C(CH_3)CONHCH_2CH_2CH_2Si(CH_3)Cl_2$ |
| | $CH_2$=$C(CH_3)CONHCH_2CH(OH)CH_2NHCH_2CH_2CH_2Si(OC_2H_5)_3$ |
| ALLYL DERIVATIVES: | $CH_2$=$CHCH_2NHCH_2CH_2CH_2Si(OCH_3)_3$ |
| | $CH_2$=$CHCH_2SiH(OCH_3)_2$ |
| | $CH_2$=$CHCH_2Si(CH_3)_2Cl$ |
| | $CH_2$=$CHCH_2SiHCl_2$ |
| | $CH_2$=$CHCH_2Si(OCH_3)_3$ |
| AMINO DERIVATIVES: | $H_2NCH_2CH_2NHCH_2CH_2CH_2Si(OCH_3)_3$(AEAPS) |
| | $H_2NCH_2CH_2CH_2CH_2CH_2CH_2NHCH_2CH_2CH_2Si(OCH_3)_3$(AHAPS) |
| | $H_2NCH_2CH_2CH_2Si(OCH_3)_3$(APS) |
| | $H_2NCH_2CH_2CH_2Si(OC_2H_5)_3$ |

TABLE I-continued

| CHEMICAL TYPE | FORMULA |
|---|---|
| EPOXY DERIVATIVES: |  $CH_2\text{—}CHCH_2OCH_2CH_2CH_2Si(OCH_3)_3$ |
| |  $CH_2\text{—}CHCH_2CH_2CH_2CH_2Si(OC_2H_5)_3$ |

In a particularly preferred embodiment, microchips having covalent attachment chemistry of the current invention use linkers denoted APS, AEAPS, AHAPS, MOTS, and AMPTS.

Figure 2:
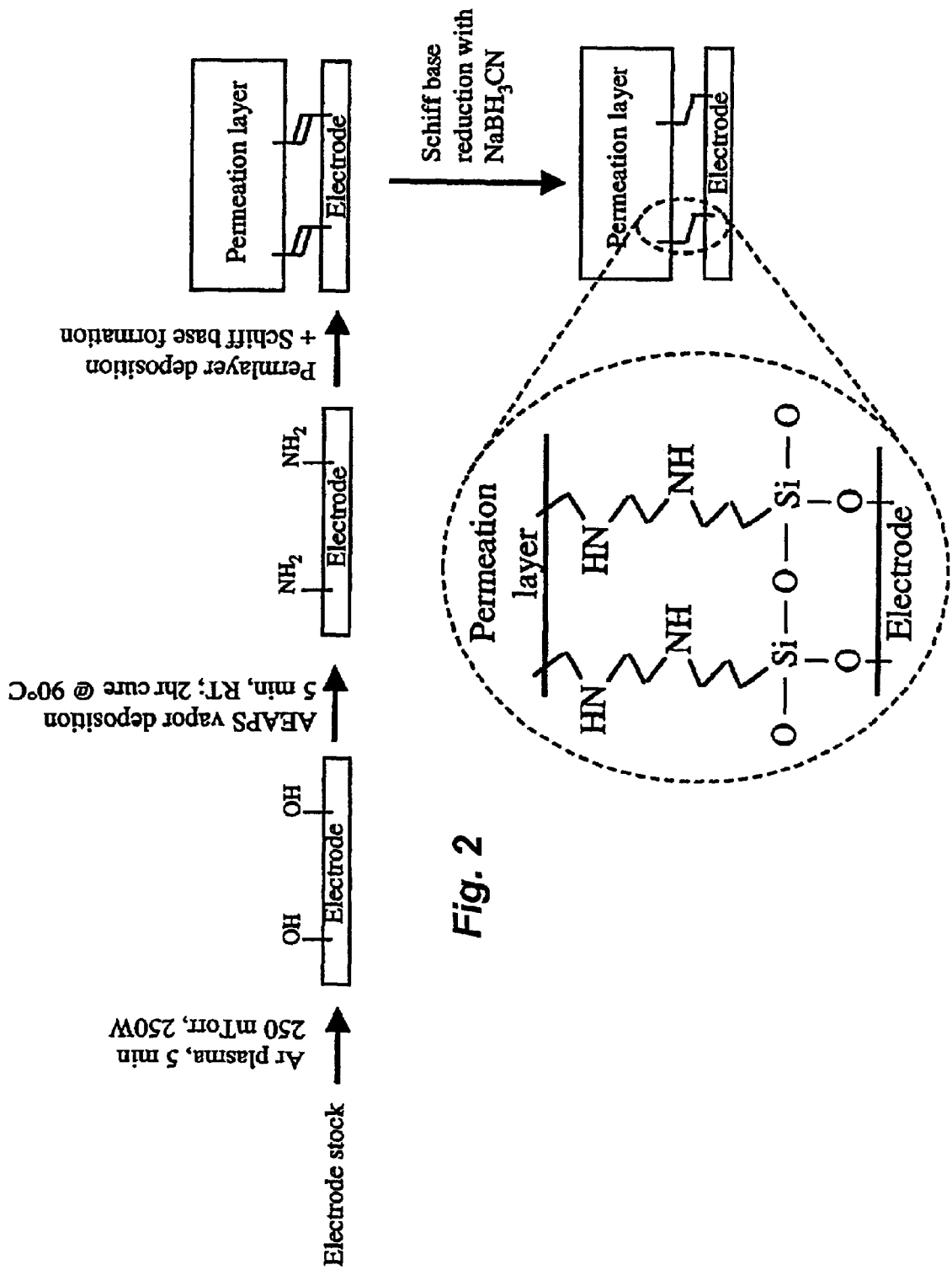
FIG. 2 is a schematic diagram showing a process for covalent attachment of the permeation layer to the electrode. In the example of the figure, the electrode is treated with an argon plasma for 5 minutes at 250 mTorr (250W). This cleans the electrode, which has hydroxyl functionalities at its surface. Linker is then attached to the electrode such as by vapor deposition for 5 minutes at room temperature followed by curing at 90° C. for 2 hours. This process leaves reactive moieties that can bond to the permeation layer. In the example of the figure, a linker having reactive amine groups is used wherein the amine moieties are available for bonding to reactive moieties of the permeation layer matrix. The bonding between the linker and permeation layer reactive centers can be accomplished using a Schiff base reaction.

FIG. 2 shows a schematic of one embodiment wherein AEAPS is used to bond the electrode to the permeation layer. In this example, the PtSi electrode microchip is first treated with an argon plasma for 5 minutes at 250 mTorr and 250 Watts. The chip is then treated with AEAPS by vapor deposition over 5 minutes at room temperature then cured onto the chip by heating for 2 hours at 90° C. This causes the linker to covalently bind to the hydroxyl groups of the silicide moiety in the PtSi electrode. Once the linker is attached to the microchip, the permeation polymer (for example glyoxylagarose) is overlaid onto the electrode surface and treated in the presence of $NaBH_3CN$ so that a Schiff base reaction and reduction can occur and cause the amine groups of the AEAPS linker to bond to the aldehyde functionality available on the permeation polymer (e.g., glyoxylagarose). Where polyacrylamide is employed as the permeation layer polymer, a UV-initiated free radical polymerization reaction can be conducted between the monomers which will make up the permeation layer and the vinyl moieties present at the surface of MOTS- or AMPTS linker-derived electrodes, thereby synthesizing the permeation layer and covalently anchoring it to the electrode in a single step.

Examples are provided below showing various delamination threasholds after attachment of the permeation layer using various linkers and attachment reaction conditions.

EXAMPLE 1

Agarose permeation layer matrix was attached to a PtSi electrode microchip following deposition of either APS or AEAPS by one of two methodologies.

APS and AEAPS were deposited by exposure of the chip to a 0.1 wt % silane/dry MeOH solution for 1 hour at room temperature. The chips were rinsed in EtOH and cured at 90° C. for 1 hour. In parallel experiments, APS and AEAPS linkers were deposited onto microchips by a vapor of neat silane in humid atmosphere for 5 min. at room temperature followed by a two hour cure at 90° C.

After the agarose permeation layer was attached, the microchips were subjected to electronic assays wherein the electrodes were biased with three direct current (DC) impulses for 2 minutes each at 200, 500, 700, and 1000 nAmps/80 μm pad (i.e., 0.04, 0.10, 0.14 and 0.20 nA/μm²) using a model 236 Source-Measure unit (Keithley Instruments Inc., Cleveland, Ohio). Following the set of three DC impulses, the electrodes were biased with a sequence of 150 negative pulses, each comprised of a 0.1 sec. ON state at −0.2 nA/μm², followed by a 0.2 sec. OFF state at 0 nA/μm². As shown in Table II, the attachment schemes using vapor deposition of the linkers provided protection from delamination up to DC impulses of 700 nA for an 80 μm electrode (0.14 nA/μm²).

TABLE II

| samp | | 200 nA DC1 | 200 nA DC2 | 200 nA DC3 | −1 uA AC | 500 nA DC1 | 500 nA DC2 | 500 nA DC3 | −1 uA AC | 700 nA DC1 | 700 nA DC2 |
|---|---|---|---|---|---|---|---|---|---|---|---|
| A | PtSi (no permlayer) | + | + | + | + | + | + | + | + | + | + |
| B | PtSi/perm layer(no linker) | + | +/− | | | +/− | − | − | − | − | − |
| C | PtSi/APS/perm layer(dry MeOH deposited)* | | | | | + | + | +/− | − | − | − |
| D | PtSi/AEAPS/ perm layer(dry MeOH deposited)* | + | + | + | + | + | +/− | − | − | − | − |
| E | PtSi/APS/perm layer(vapor deposited)* | | | | | + | + | + | + | + | +/− |

TABLE II-continued

| samp | | 200 nA DC1 | 200 nA DC2 | 200 nA DC3 | -1 uA AC | 500 nA DC1 | 500 nA DC2 | 500 nA DC3 | -1 uA AC | 700 nA DC1 | 700 nA DC2 |
|---|---|---|---|---|---|---|---|---|---|---|---|
| F | PtSi/AEAPS/ perm layer(vapor deposited)* | | | | | + | + | + | + | + | +/- |

Figure 3A:
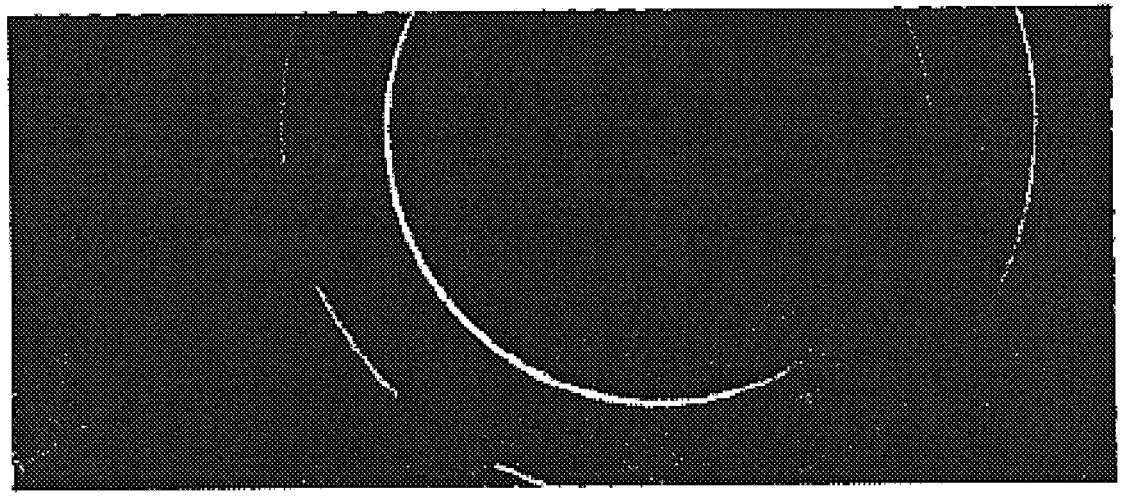
FIGS. 3A and B are confocal microscope photos of partial images of individual electrodes wherein the permeable membrane attached to the electrode surface without use of a linker moiety is shown before (A) and after (B) delamination.
Figure 3B:
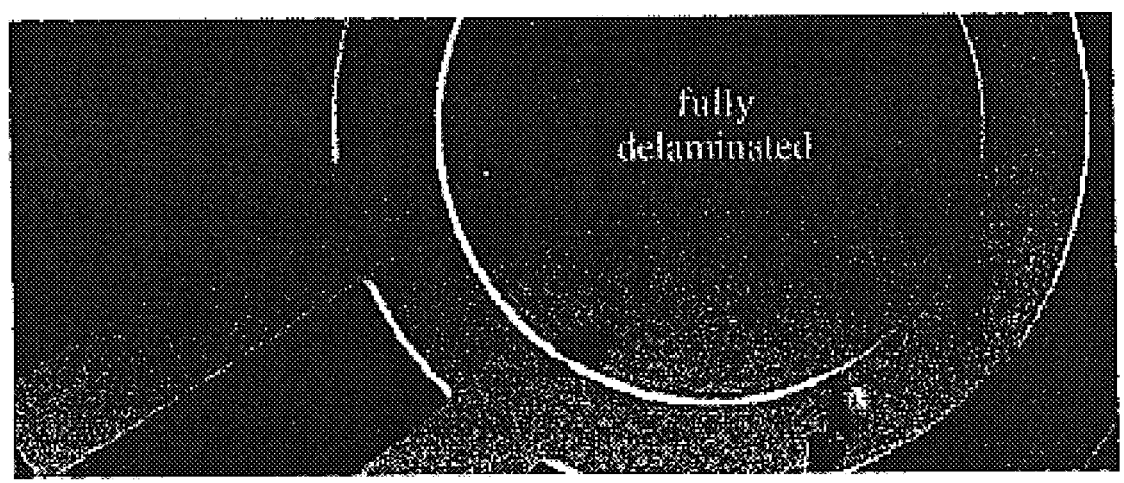
Figure 4A:
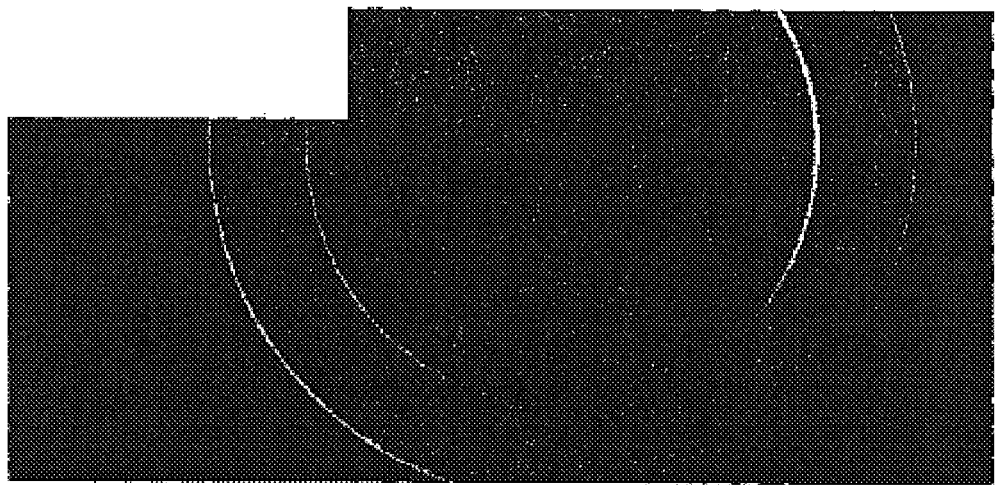
FIGS. 4A–D are confocal microscope photos of partial images of individual electrodes wherein the permeable membrane attached to the electrode surface using AEAPS deposited by vapor is shown at various degrees of delamination.
Figure 4B:
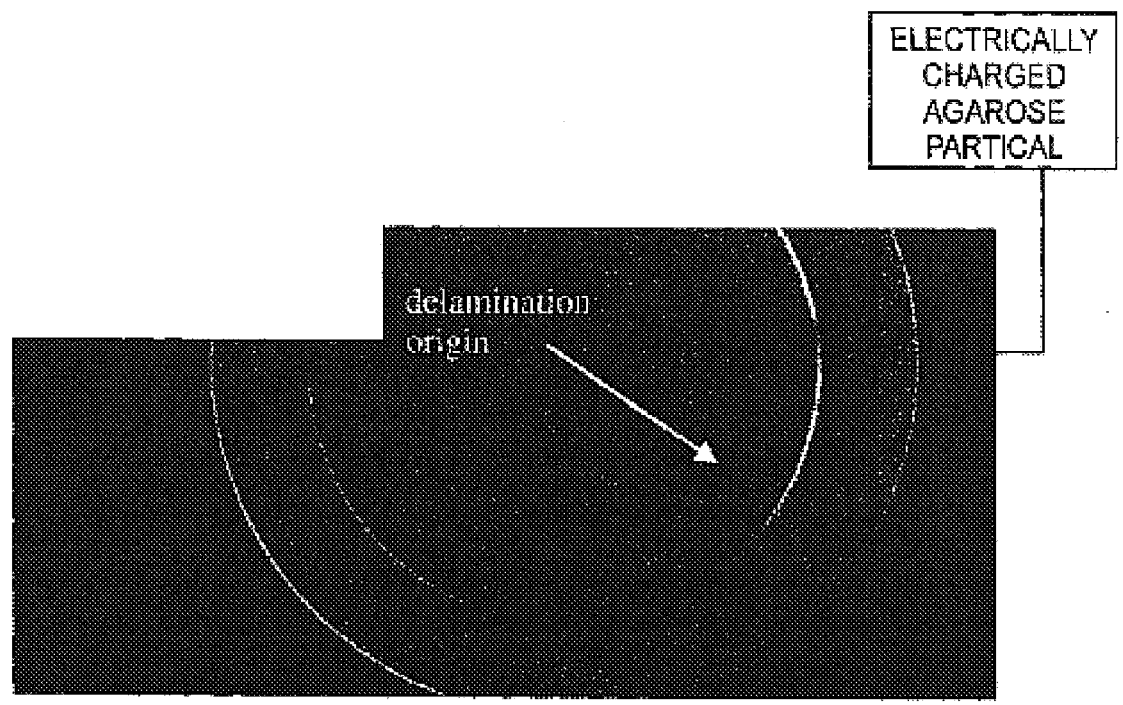
Figure 4C:
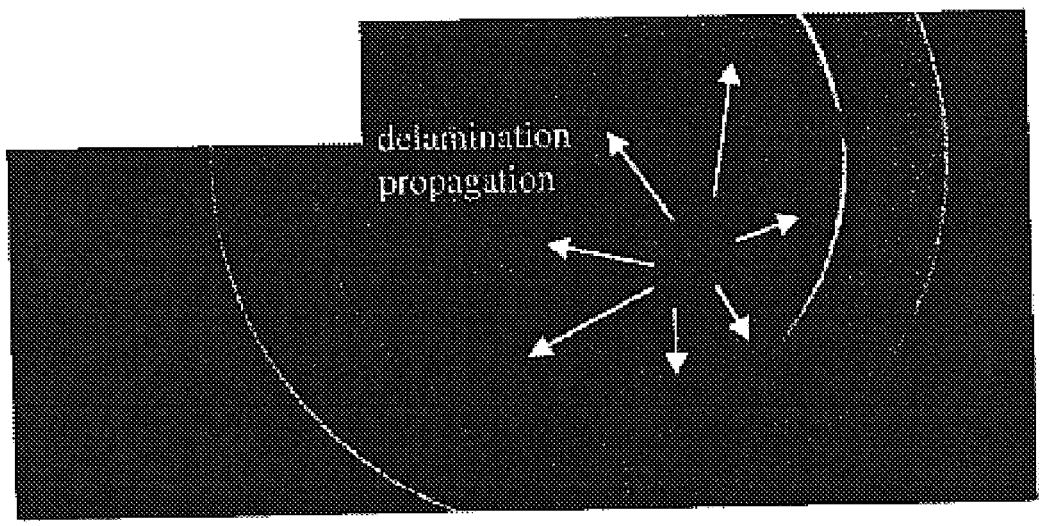
Figure 4D:
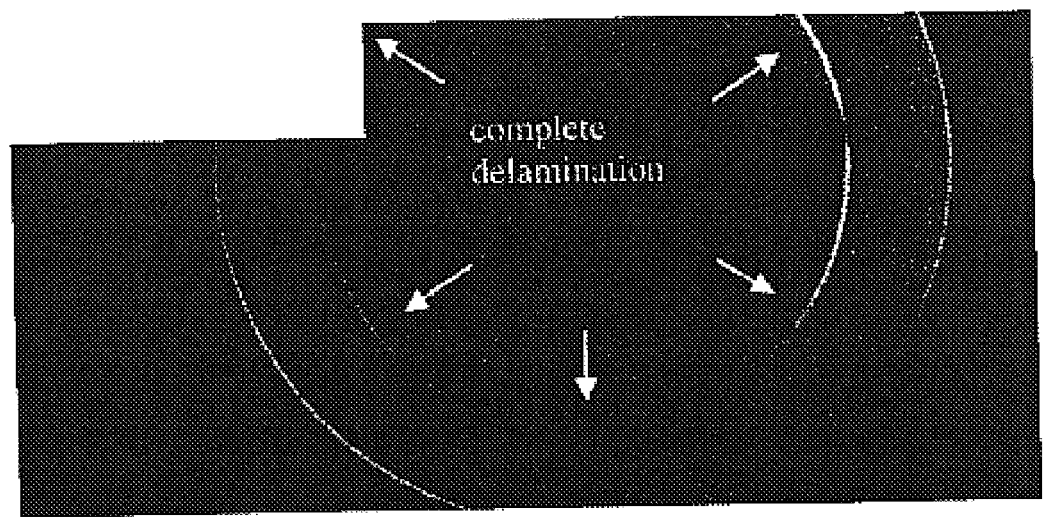

+ = no delamination
+/- = initial indication of delamination
− = delamination resulting in decoupling of layer from pad.
* = the method of deposition applies to the silane, not the permeation layer As shown in FIGS. 3 and 4, delamination will occur at low levels of DC (200 nA (0.04 nA/$\mu$m$^2$) after second DC pulse) where no covalent linker attachment is used to anneal the permeation layer to the electrode (FIGS. 3A and B). Conversely, where AEAPS is used that has been applied to the electrode using vapor deposition, the delamination does not appear until the electrode has been exposed to the second DC pulse at 700 nA (0.14 nA/$\mu$m$^2$) (delamination extended to 25% of the pad area at 3 min. past shut-off) with complete delamination by 2 minutes past third DC shut-off (FIGS. 4A–D).

EXAMPLE 2

In this example, delamination of the permeation layer from the electrode was tested using a multilayer permeation layer wherein the layers were applied using spin coating techniques then reacted to cause the linking moieties to covalently bond the layers together and to the electrode.

Specifically, microchips having PtSi electrodes were cleaned with oxygen plasma for 10 minutes followed by argon plasma for 10 minutes. AEAPS was then vapor-deposited for 5 minutes followed by curing at 90° C. under vacuum. Subsequently, a first layer solution comprising 2.5% glyoxylagarose solution (NuFix) which had been stirred for 10 minutes at room temperature then boiled 7 minutes followed by filtering at 1.2 $\mu$m into the ASC device reservoir at 65° C., was spin-deposited onto the microchips with an automatic spin-coating device (ASC). Following deposition of the first layer, a second layer, comprising streptavidin (Scripps Laboratory, San Diego) at 5 mg/ml in 10 mM sodium phosphate, 250 mM NaCl (pH 7.2) which was filtered at 0.2 $\mu$m into the ASC reservoir and maintained at room temperature, was deposited similarly. The bottom layer was spin-coated at either 1500 or 2500 rpm, while the top layer was spin-coated at 5,000 rpm. The reaction for the reduction of the Schiff bases generated between streptavidin and glyoxylagarose, and between the AEAPS surface and glyoxylagarose was carried out by treating the coated microchip with 0.2 M NaBH$_3$CN 0.1 M sodium phosphate (pH 7.4) for 1 hr. at room temperature. Capping of the unreacted sites was performed by application of 0.1 M Gly/0.1 M NaBH$_3$CN, 0.1 M sodium phosphate (pH 7.4) to the chip for 30 minutes at room temperature. Finally, the treated microchip was exhaustively rinsed and soaked in deionized water for 30 minutes and then air dried overnight at room temperature.

As shown in Table III below, the thickness of the double permeation layer was examined where the substrate contained either plain platinum electrodes or PtSi electrodes using two different rotational speeds for the bottom layer deposition. The results indicate that spin-coating results in deposition of permeation layers of variable thicknesses.

TABLE III

| Microchip type | Bottom layer spun at 1.5K rpm, bilayer thickness in nanometers | Bottom layer spun at 2.5K rpm, bilayer thickness in nanometers |
|---|---|---|
| Pt/AEAPS/ agarose | 587 ± 4<br>668 ± 4<br>668 ± 3 | 465 ± 4<br>465 ± 4<br>— |
| PtSi/AEAPS/ agarose | 744 ± 17<br>685 ± 1 | 511 ± 4<br>620 ± 5<br>494 ± 90 |

Figure 5A:
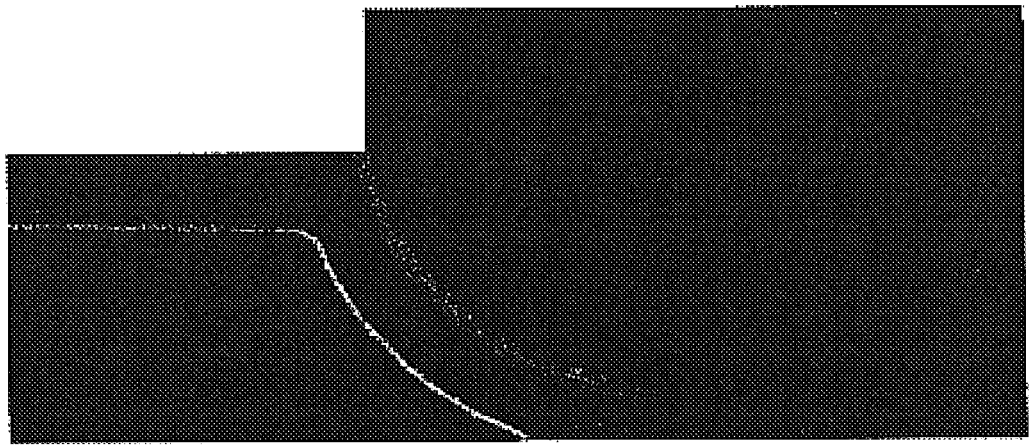
FIGS. 5A and B are confocal microscope photos of partial images of 80 $\mu$m diameter Pt (A) and a PtSi (B) electrodes wherein the permeable membrane was attached to the electrode surface using AEAPS.
Figure 5B:
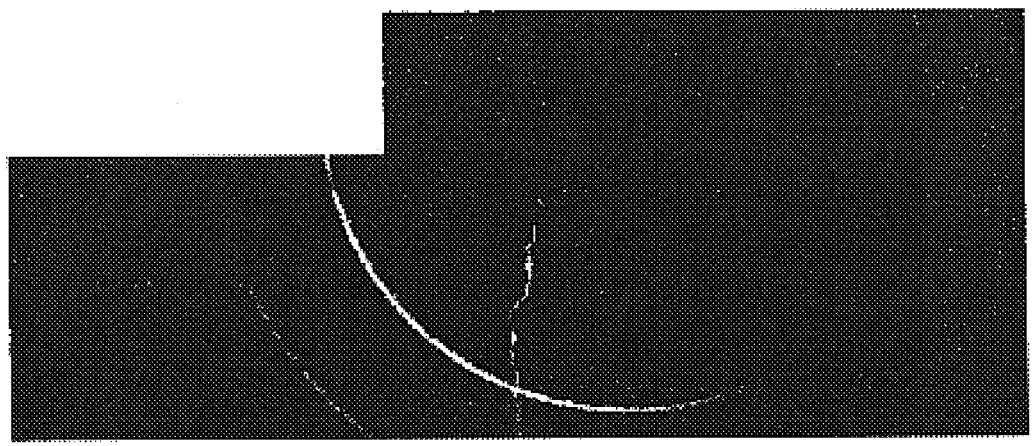

The chips as fabricated in this example, were tested for resistance to delamination. For the platinum electrode microchips, 9 electrode pads were individually addressed from two separate chips in 50 mM fresh Histidine buffer. These pads showed consistent delamination past the second two-minute direct current pulse of 500 nA/80 $\mu$m pad (0.1 nA/$\mu$m$^2$) (FIG. 5A). In contrast, 6 pads were individually addressed from 2 of the PtSi microchips under the same conditions. These PtSi pads had no delamination up to several $\mu$A/pad (FIG. 5B). Thus, the PtSi electrode using the AEAPS attachment linker provided protection from delamination.

EXAMPLE 3

In this example, data is presented showing that the covalent attachment method of the invention using PtSi electrodes, agarose and aminopropylsilanes also protects against delamination of the permeation layer under alternating current conditions. Here, Pt and PtSi microchips bonded to the permeation layer with AEAPS were tested using two pulsed biasing protocols.

Both protocols were carried out using 50 mM L-Histidine buffer. Specifically, in protocol A, the microchips were biased at +800 nA/pad (0.16 nA/$\mu$m$^2$) for 38 milliseconds (ms), −800 nA/pad for 25 ms, cycled for a total of 25 seconds using 3 pads each pulse. In protocol B, the microchips were biased at +1.6 $\mu$A/pad (0.32 nA/$\mu$m$^2$) for 19 ms, −1.6 $\mu$A/pad for 12 ms, and cycled for a total of 14 seconds each on 3 pads addressed simultaneously. Images were taken using an INM 100 confocal microscope (Leica).

Figure 6A:
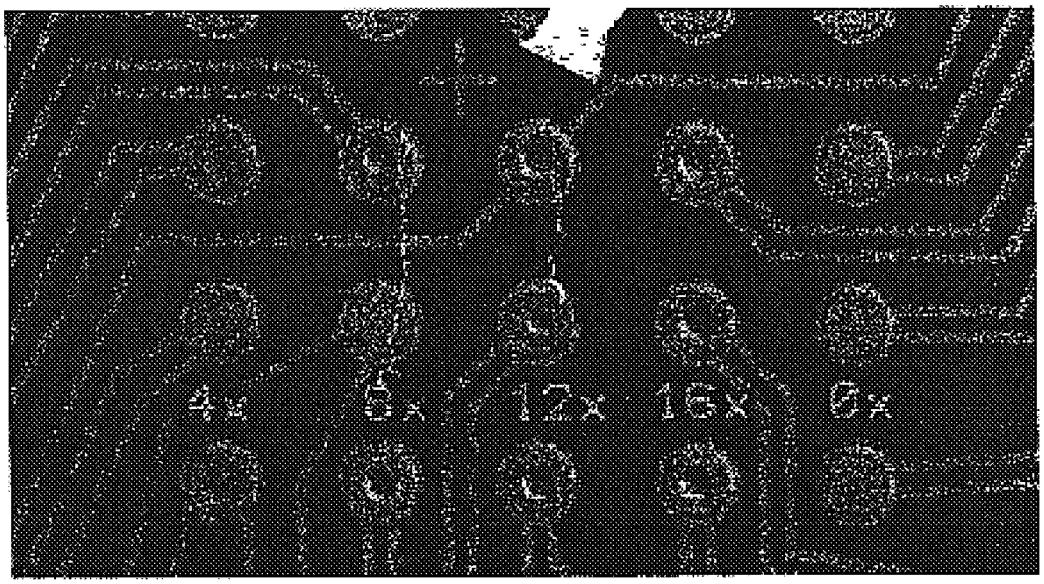
FIGS. 6A and B, and 7A and B are confocal microscope photos of partial images of electrode arrays wherein the permeable membrane was either deposited on a Pt electrode without chemical attachment (6A and 7A) or was attached to a PtSi electrode surface using AEAPS (6B and 7B). The images show the levels of repeated biasing that result in delamination for Pt without covalent bonding of the permeation layer and PtSi microchips with covalent bonding.
Figure 6B:
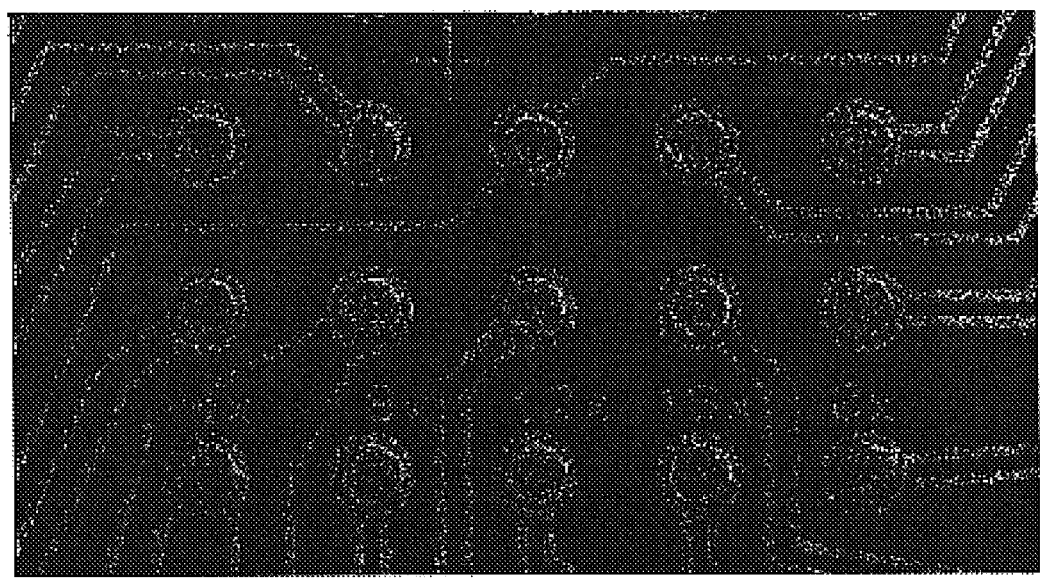
Figure 7A:
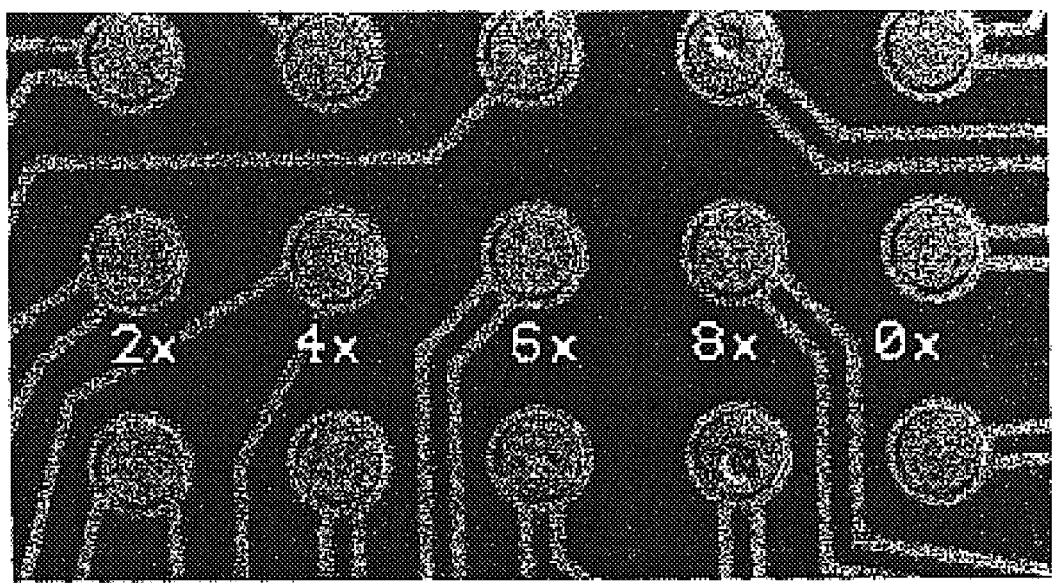
Figure 7B:
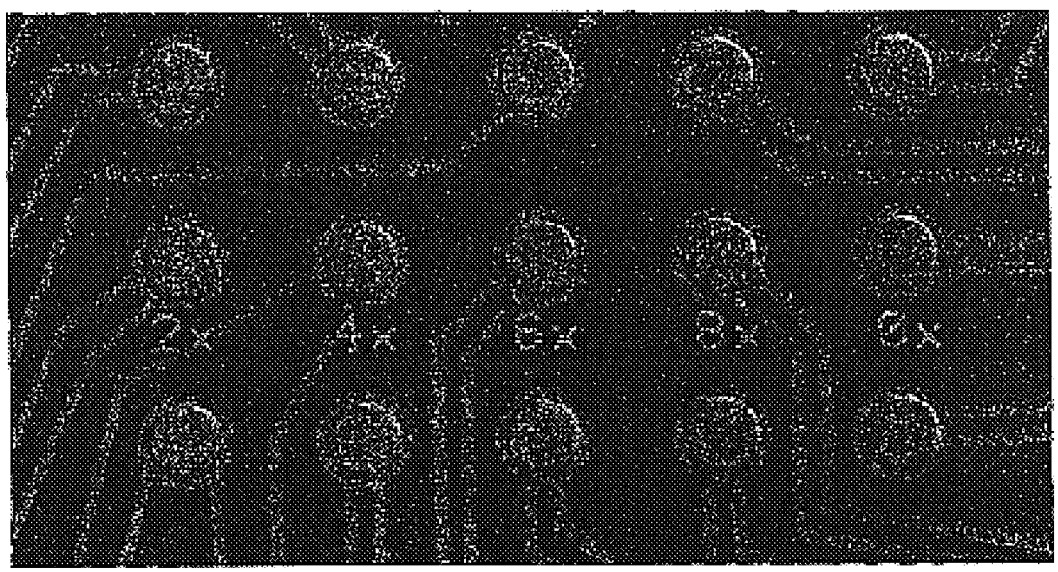

FIG. 6A shows Pt chips that were biased using protocol A, followed by 0, 4, 8, 12 or 16 repeats of protocol B. The images show that delamination begins after 8 repeats of protocol B. In contrast, the PtSi chips (FIG. 6B) showed delamination to a much less extent at the 8$^{th}$ biasing. In order to more accurately define the delamination threshold, the chips were assayed with smaller stringency increments using biasing repeats of 2, 4, 6, and 8 times. On Pt electrodes, delamination began to occur at bias repeat number 6 (FIG. 7A). In contrast, the PtSi chip showed less delamination effect at the same level of electrodynamic stress (FIG. 7B).

The overall results indicate that damage begins to occur during the sixth application of the above protocol B and that the delamination increased with increasing cycle repeats. This delamination effect was less prominent in the PtSi chips.

EXAMPLE 4

In this example, methacryloylsilanes are employed as linkers for attaching synthetic permeation layers such as acrylamide-based hydrogels to Pt and PtSi chips. Additionally, the integrity of the permeation layer was examined using a technique wherein glass beads are applied to the surface of the permeation layer as a reference upon which the confocal microscope can focus. This enables permeation layer thickness determination and facilitates the monitoring of permeation layer distortions due to such things as delamination.

Figure 8:
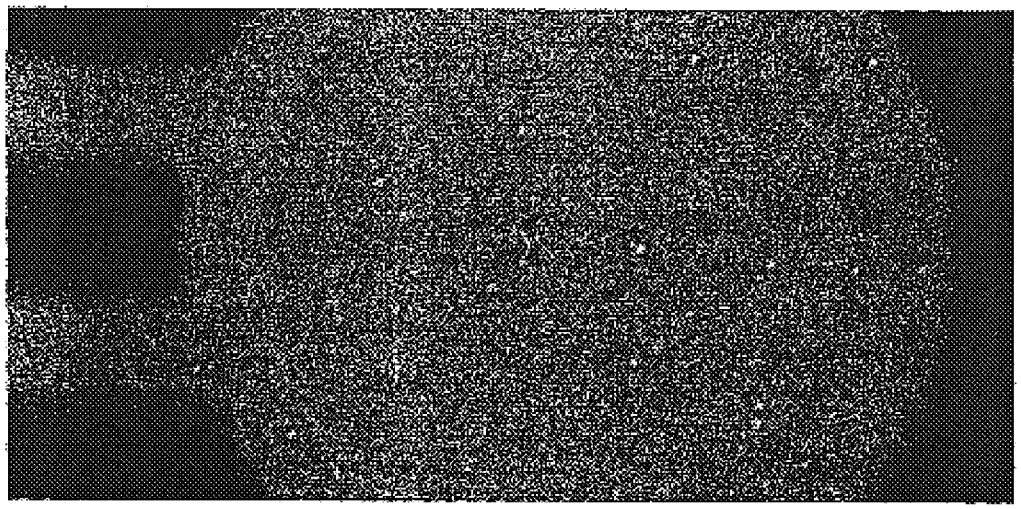
FIGS. 8, 9, and 10 are confocal microscope photos of partial images of a Pt electrode overlaid with agarose.
Figure 9:
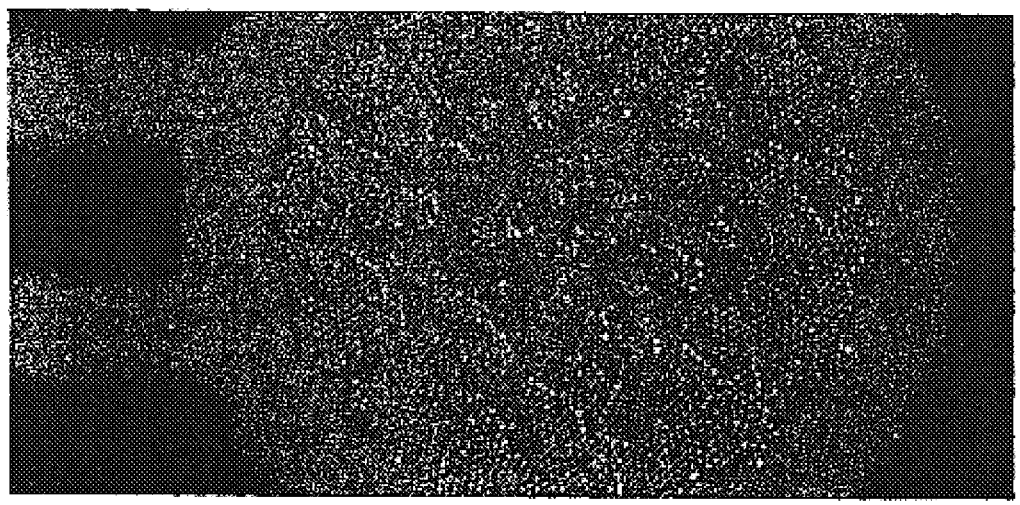
Figure 10:
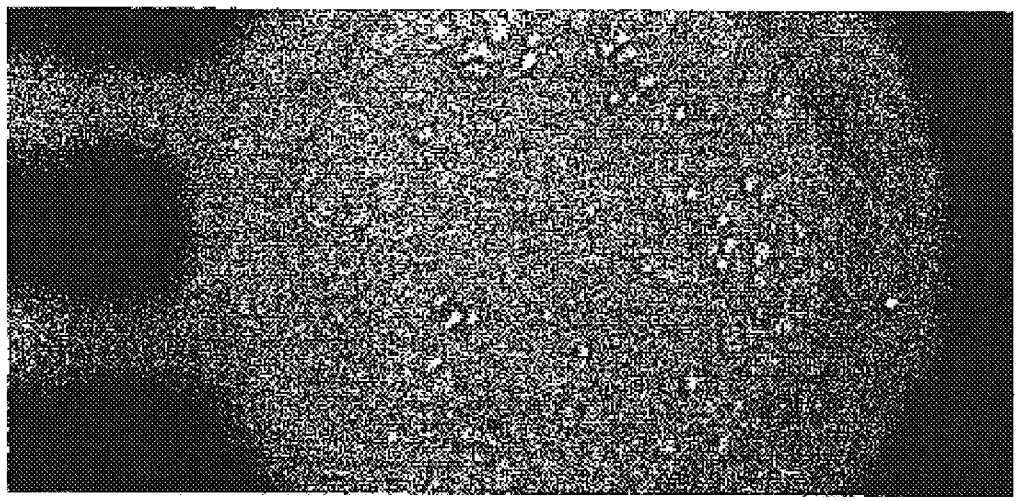
Figure 11:
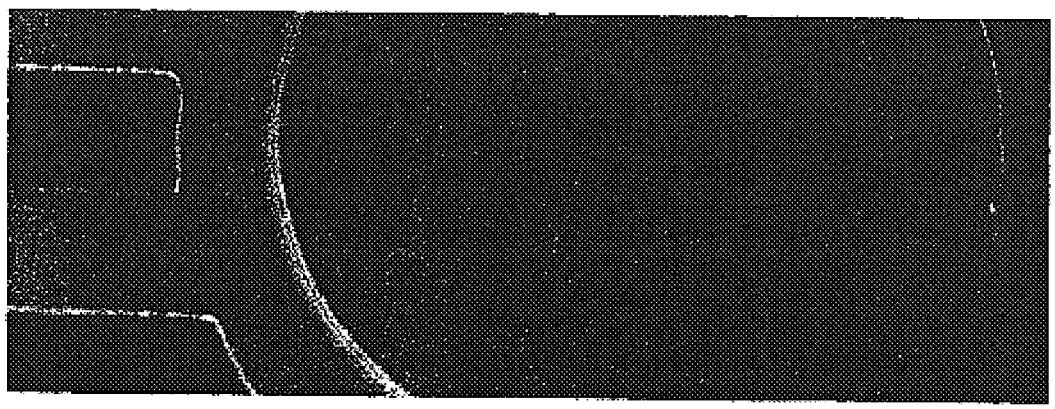
FIG. 11 is a confocal microscope photo showing confirmation that the permeation layer of FIG. 10 delaminated as indicated by the presence of concentric rings.

FIG. 8 shows a Pt microchip having an agarose permeation layer wherein the thickness of the layer before electronic biasing was determined to be 3.0±0.5 $\mu$m. The figure shows the focal point at the position of the beads above the electrode. Thus, the underlying electrode is slightly out of focus. FIG. 9, the same electrode during a bias at +200 nA (0.04 nA/$\mu$m$^2$) with direct current without observable distortion of the permeation layer. The beads migrate to the electrode due to the positive bias. Following this two-minute bias, the impulse was terminated and the electrode observed for changes in its appearance. As seen in FIG. 10, the beads resting over the center of the electrode moved to a location 4.0±0.5 $\mu$m above the electrode based on the vertical shift required to bring said beads back into the focal plane. Thus, the permeation layer underwent a 1 $\mu$m expansion. As shown in FIG. 11, this expansion appears to be related to the delamination of the permeation layer from the electrode (microdelamination) as indicated by the presence of concentric rings visible at the edges of the electrode pad. Additionally, in other experiments, not shown, we have observed permeation layer thickness distortions from 2 to 6 $\mu$m occurring with delamination.

Figure 12:
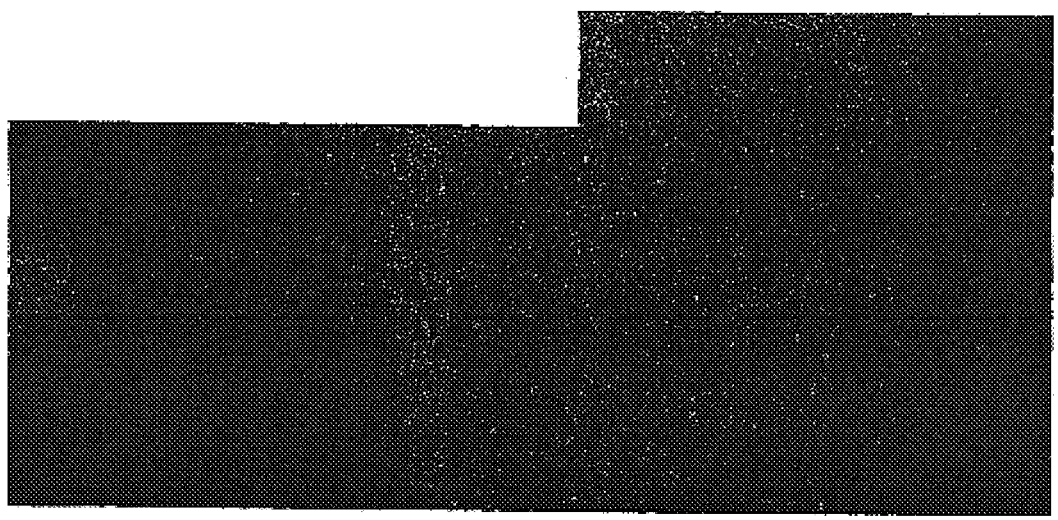
FIGS. 12 and 13 are confocal microscope photos of partial images of electrodes showing PtSi electrode with an acrylamide permeation layer covalently attached.
Figure 13:
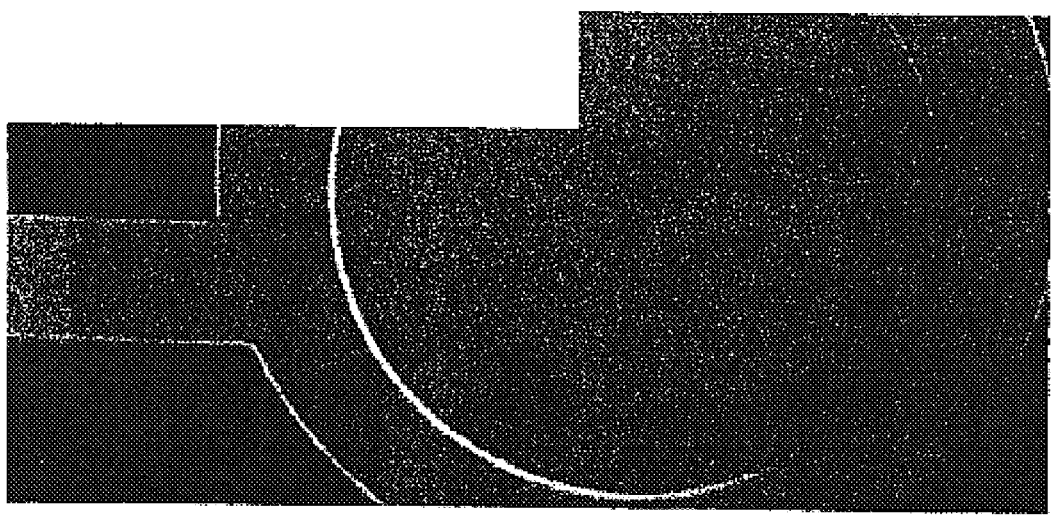

In another experiment, acrylamide-based hydrogel permeation layers anchored to PtSi electrodes via the MOTS linker were exposed to a +200 nA (0.04 nA/$\mu$m$^2$) bias for 2 minutes and examined for delamination. FIG. 12 shows beads resting atop the permeation layer 6 $\mu$m above the electrode surface. The beads remained at the same position above the electrode after bias shut-off, indicating that no distortion of the permeation layer occurred. FIG. 13 shows the same pad with the focal point positioned at the electrode. No delamination ringlets were observed. When the electrodynamic stress was increased to +5 $\mu$A (1 nA/$\mu$m$^2$) for 2 mins., the permeation layer was observed to distort such that the layer seemed to swell. However, no delamination from the electrode was observed. The results of the above experiments are shown in Table IV.

TABLE IV

| chip type | bias conditions (current densities) | dry thickness | initial wet thickness | post address distortion | integrity of electrode/ permeation layer bond |
|---|---|---|---|---|---|
| Pt/agarose | 200nA, 2 min (0.04 nA/$\mu$m$^2$) | 0.80 ± 0.01 | 3.0 ± 0.5 | 4.0 ± 0.5 | delamination & distortion |
|  | 200nA, 2 min (0.04 nA/$\mu$m$^2$) | 0.80 ± 0.01 | 3.0 ± 0.5 | 6.0 ± 0.5 | delamination & distortion |
| Pt/poly acrylamide | 200nA, 2 min (0.04 nA/$\mu$m$^2$) | 2.0 ± 0.1 | 5.0 ± 0.5 | 9.0 ± 0.5 | delamination & distortion |
|  | 200nA, 2 min (0.04 nA/$\mu$m$^2$) | 1.9 ± 0.1 | 5.0 ± 0.5 | 9.0 ± 0.5 | delamination & distortion |
| PtSi/poly acrylamide | 200nA, 2 min (0.04 nA/$\mu$m$^2$) | 2.0 ± 0.1 | 5.0 ± 0.5 | 5.0 ± 0.5 | intact |
|  | 500nA, 1 min (0.1 nA/$\mu$m$^2$) | 2.0 ± 0.1 | 6.0 ± 0.5 | 6.0 ± 0.5 | intact |
|  | 1 uA, 2 min (0.2 nA/$\mu$m$^2$) | 2.0 ± 0.1 | 6.0 ± 0.5 | 6.0 ± 0.5 | intact |
|  | 2 uA, 2 min (0.4 nA/$\mu$m$^2$) | 2.0 ± 0.1 | 6.0 ± 0.5 | 6.0 ± 0.5 | intact |
|  | 5 uA, 2 min (1 nA/$\mu$m$^2$) | 2.0 ± 0.1 | 6.0 ± 0.5 | 12.0 ± 0.5 | distortion without delamination |

Given that these results show that current densities in the range of 1 nA/$\mu$m$^2$ are useful in the operation of microchips having bonding chemistry resistant to delamination, we further contemplate that current densities in the range of at least 10 nA/$\mu$m$^2$ may be used with microchips having permeation layers which are bound to the electrodes using the bonding chemistry of the present invention without delamination.

Modifications and other embodiments of the invention will be apparent to those skilled in the art to which this invention relates having the benefit of the foregoing teachings, descriptions, and associated drawings. The present invention is therefore not to be limited to the specific embodiments disclosed but is to include modifications and other embodiments which are within the scope of the appended claims. All references are herein incorporated by reference.

We claim:

1. A device comprising a plurality of microlocations:
   wherein the microlocations each comprise an underlying working microelectrode on a substrate, wherein the microelectrode comprises platinum silicide (PtSi),
   wherein at least some of the microelectrodes are covered by a permeation layer,
   further wherein at at least one microlocation the permeation layer is covalently attached to the electrode by linker moieties,
   and wherein the covalent attachment between the electrode and the linker and the permeation layer material is stable at a current density of at least 0.10 nA/$\mu$m$^2$.

2. The device of claim 1 wherein the permeation layer comprises a material selected from the group consisting of an inorganic sol-gel, a synthetic polymer hydrogel, and a carbohydrate hydrogel.

3. The device of claim 1 wherein the linker has the formula $$\text{X-SPACER} - \underset{\underset{(C)}{\diagdown}}{\overset{\overset{(A)}{\diagup}}{\text{Si}}} - (B)$$

wherein:

X is selected from the group consisting of acrylate, methacrylate, acrylamide, methacrylamide, allyl, vinyl, acetyl, amine, substituted amine, epoxy and thiol;

SPACER is selected from the group consisting of alkyl, aryl, mono- or polyalkoxy, ethyleneglycol, polyethyleneglycol, mono- or polyalkylamine, mono- or polyamide, thioether derivatives, and mono- or poly-disulfides;

A and B are selected from the group consisting of Oxygen-R, Cl, Br, and an X-SPACER moiety, or any combination thereof, wherein R is H, alkyl, methyl, ethyl, propyl, isopropyl, and branched or linear alkyl of 4 to 10 carbon atoms; and C is a hydrolyzable moiety selected from the group consisting of Oxygen-R, Cl, and Br, wherein R is H, branched alkyl, methyl, ethyl, propyl, isopropyl, and branched or linear alkyl of 4 to 10 carbon atoms.

4. The device of claim 3 wherein the linker is selected from the group consisting of:

$H_2NCH_2CH_2CH_2CH_2Si(OCH_3)_3$), $H_2NCH_2CH_2NHCH_2CH_2CH_2Si(OCH_3)_3$, $H_2NCH_2CH_2CH_2CH_2CH_2NHCH_2CH_2CH_2Si(OCH_3)_3$, $CH_2=C(CH_3)COOCH_2CH_2CH_2Si(OCH_3)_3$, and $CH_2=CHCONHCH_2CH_2CH_2Si(OC_2H_5)_3$.

5. The device of claim 1 wherein the permeation layer is a hydrogel comprising a material selected from the group consisting of: agarose, glyoxylagarose, acrylamide, methacrylamide, polyacrylamide, and other synthetic polymers.

6. The device of claim 5 wherein the hydrogel comprises glyoxylagarose.

7. The device of claim 5 wherein the hydrogel comprises polyacrylamide.

8. The device of claim 1 wherein the electrode is a metal/silicide electrode selected from the group consisting of platinum suicide (PtSi), tungsten suicide (WSi), titanium silicide (TiSi), and gold suicide (AuSi).

9. The device of claim 1 wherein the electrode is a metal/metal electrode selected from the group consisting of platinum/titanium (PtTi) and gold/titanium (AuTi).

10. The device of claim 1 wherein the electrode is an organic electrode selected from the group consisting of poly(phenylene vinylene), polythiophene, and polyaniline.

11. The device of claim 3 wherein the linker is an acrylate linker selected from the group consisting of:

$CH_2=CHCOOCH_2CH_2CH_2Si(OCH_3)_3$, $CH_2=CHCOOCH_2CH_2CH_2SiCl_3$, $CH_2=CHCOOCH_2CH_2CH_2Si(CH_3)(OCH_3)_2$, $CH_2=CHCOOCH_2CH_2CH_2Si(CH_3)_2(OCH_3)$, $CH_2=CHCOOCH_2CH_2CH_2Si(CH_3)Cl_2$, and $CH_2=CHCOOCH_2CH(OH)CH_2NHCH_2CH_2CH_2Si(OC_2H_5)_3$.

12. The device of claim 3 wherein the linker is a methacrylate linker selected from the group consisting of:

$CH_2=C(CH_3)COOCH_2CH_2CH_2Si(OCH_3)_3$, $CH_2=C(CH_3)COOCH_2CH_2CH_2SiCl_3$, $CH_2=C(CH_3)COOCH_2CH_2CH_2Si(CH_3)(OCH_3)_2$, $CH_2=C(CH_3)COOCH_2CH_2CH_2Si(CH_3)_2(OCH_3)$, $CH_2=C(CH_3)COOCH_2CH_2CH_2Si(CH_3)Cl_2$, and $CH_2=C(CH_3)COOCH_2CH(OH)CH_2NHCH_2CH_2CH_2Si(OC_2H_5)_3$.

13. The device of claim 3 wherein the linker is an acrylamide linker selected from the group consisting of;

$CH_2=CHCONHCH_2CH_2CH_2Si(OC_2H_5)_3$, $CH_2=CHCONHCH_2CH_2CH_2SiCl_3$, $CH_2=CHCONHCH_2CH_2CH_2Si(CH_3)(OCH_3)_2$, $CH_2=CHCONHCH_2CH_2CH_2Si(CH_3)_2(OCH_3)$, $CH_2=CHCONHCH_2CH_2CH_2Si(CH_3)Cl_2$, $CH_2=CHCONHCH_2CH(OH)CH_2NHCH_2CH_2CH_2Si(OC_2H_5)_3$, and $CH_2=CHCONHCH_2CH_2CONHCH_2CH_2CONHCH_2CH_2Si(OC_2H_5)_3$.

14. The device of claim 3 wherein the linker is a methacrylamide linker selected from the group consisting of:

$CH_2=C(CH_3)CONHCH_2CH_2CH_2Si(OCH_3)_3$, $CH_2=C(CH_3)CONHCH_2CH_2CH_2SiCl_3$, $CH_2=C(CH_3)CONHCH_2CH_2CH_2Si(CH_3)(OCH_3)_2$, $CH_2=C(CH_3)CONHCH_2CH_2CH_2Si(CH_3)_2(OCH_3)$, $CH_2=C(CH_3)CONHCH_2CH_2CH_2Si(CH_3)Cl_2$, and $CH_2=C(CH_3)CONHCH_2CH(OH)CH_2NHCH_2CH_2CH_2Si(OC_2H_5)_3$.

15. The device of claim 3 wherein the linker is an allyl derivative linker selected from the group consisting of:

$CH_2=CHCH_2NHCH_2CH_2CH_2Si(OCH_3)_3$, $CH_2=CHCH_2SiH(OCH_3)_2$, $CH_2=CHCH_2Si(CH_3)_2Cl$, $CH_2=CHCH_2SiHCl_2$, and $CH_2=CHCH_2Si(OCH_3)_3$.

16. The device of claim 3 wherein the linker is an amino derivative linker selected from the group consisting of:

$H_2NCH_2CH_2NHCH_2CH_2CH_2Si(OCH_3)_3$, $H_2NCH_2CH_2CH_2CH_2CH_2CH_2NHCH_2CH_2CH_2Si(OCH_3)_3$, $H_2NCH_2CH_2CH_2Si(OCH_3)_3$, and $H_2NCH_2CH_2CH_2Si(OC_2H_5)_3$.

17. The device of claim 3 wherein the linker is an epoxy derivative linker selected from the group consisting of:

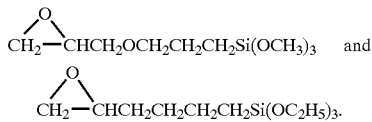

18. The device of claim 4 wherein the linker is $H_2NCH_2CH_2CH_2Si(OCH_3)_3$.

19. The device of claim 4 wherein the linker is $H_2NCH_2CH_2NHCH_2CH_2CH_2Si(OCH_3)_3$.

20. The device of claim 4 wherein the linker is $CH_2\!=\!C(CH_3)COOCH_2CH_2CH_2Si(OCH_3)_3$.

21. The device of claim 1 wherein the resulting covalent attachment between the electrode and the linker and the permeation layer material is stable at a current density of at least 0.2 $nA/\mu m^2$.

22. The device of claim 1 wherein the resulting covalent attachment between the electrode and the linker and the permeation layer material is stable at a current density of at least 0.4 $nA/\mu m^2$.

* * * * *

UNITED STATES PATENT AND TRADEMARK OFFICE
CERTIFICATE OF CORRECTION

PATENT NO. : 6,838,053 B2
DATED : January 4, 2005
INVENTOR(S) : Havens, John R. et al.

It is certified that error appears in the above-identified patent and that said Letters Patent is hereby corrected as shown below:

Title page,
Item [54], Title, delete "MICROLOCAIONS", and insert -- MICROLOCATIONS --
Item [75], Inventors, delete "Havens R. John", and insert -- John R. Havens --

Signed and Sealed this

Nineteenth Day of April, 2005

JON W. DUDAS
*Director of the United States Patent and Trademark Office*